(12) United States Patent
Babcock et al.

(10) Patent No.: US 10,724,351 B2
(45) Date of Patent: *Jul. 28, 2020

(54) SYSTEMS AND METHODS OF OPTIMIZING Y-GRADE NGL ENHANCED OIL RECOVERY FLUIDS

(71) Applicants: Linde Aktiengesellschaft, Munich (DE); John A. Babcock, Houston, TX (US)

(72) Inventors: John A. Babcock, Houston, TX (US); Charles P. Siess, III, Conroe, TX (US); Kevin G. Watts, Spring, TX (US)

(73) Assignee: Linde Aktiengesellschaft, Munich (DE)

( * ) Notice: Subject to any disclaimer, the term of this patent is extended or adjusted under 35 U.S.C. 154(b) by 168 days.

This patent is subject to a terminal disclaimer.

(21) Appl. No.: 15/680,864

(22) Filed: Aug. 18, 2017

(65) Prior Publication Data

US 2019/0055824 A1 Feb. 21, 2019

(51) Int. Cl.
| | | |
|---|---|---|
| *E21B 43/16* | (2006.01) | |
| *C09K 8/584* | (2006.01) | |
| *C09K 8/594* | (2006.01) | |
| *E21B 43/40* | (2006.01) | |
| *E21B 47/00* | (2012.01) | |
| *C09K 8/588* | (2006.01) | |

(Continued)

(52) U.S. Cl.
CPC .......... *E21B 43/164* (2013.01); *C09K 8/584* (2013.01); *C09K 8/588* (2013.01); *C09K 8/594* (2013.01); *C09K 8/92* (2013.01); *C10G 5/06* (2013.01); *C10G 70/041* (2013.01); *E21B 43/166* (2013.01); *E21B 43/40* (2013.01); *E21B 47/00* (2013.01); *G01N 33/225* (2013.01); *G05B 17/00* (2013.01); *C09K 2208/30* (2013.01)

(58) Field of Classification Search
CPC .... C09K 2208/10; C09K 8/584; C09K 8/594; C09K 8/94; C09K 8/64; C09K 8/82; E21B 43/16; E21B 43/164; E21B 43/166; E21B 43/267; E21B 47/00; E21B 43/255
See application file for complete search history.

(56) References Cited

U.S. PATENT DOCUMENTS

| | | |
|---|---|---|
| 3,035,637 A | 5/1962 | Allen |
| 3,316,965 A | 5/1967 | Watanabe |

(Continued)

FOREIGN PATENT DOCUMENTS

| | | |
|---|---|---|
| CN | 201885591 U | 6/2011 |
| DE | 102014010105 A1 | 1/2016 |

(Continued)

OTHER PUBLICATIONS

Australian Examination Report dated Oct. 4, 2017, corresponding to Application No. 2015336280.

(Continued)

*Primary Examiner* — Zakiya W Bates
(74) *Attorney, Agent, or Firm* — Patterson + Sheridan, LLP (57) ABSTRACT

Systems and methods of optimizing enhanced oil recovery fluids in the form of a hydrocarbon foam, an emulsion based foam, an emulsion, and a gelled enhanced oil recovery fluid, each comprising Y-Grade NGL, which is an unfractionated hydrocarbon mixture that comprises ethane, propane, butane, isobutane, and pentane plus, wherein the unfractionated hydrocarbon mixture is a byproduct of a condensed and demethanized hydrocarbon stream.

50 Claims, 5 Drawing Sheets

(51) Int. Cl.
*C09K 8/92* (2006.01)
*C10G 5/06* (2006.01)
*C10G 70/04* (2006.01)
*G01N 33/22* (2006.01)
*G05B 17/00* (2006.01)

(56) References Cited

U.S. PATENT DOCUMENTS

| | | | |
|---|---|---|---|
| 3,319,712 | A | 5/1967 | O'Brien |
| 3,368,627 | A | 2/1968 | Hurst et al. |
| 4,490,985 | A | 1/1985 | Wells |
| 4,511,381 | A | 4/1985 | Mehra |
| 4,576,005 | A | 3/1986 | Force |
| 6,230,814 | B1 | 5/2001 | Nasr et al. |
| 7,373,790 | B2 | 5/2008 | Clare et al. |
| 7,527,096 | B2 | 5/2009 | Chung et al. |
| 8,505,332 | B1 | 8/2013 | Prim |
| 8,844,639 | B2 | 9/2014 | Gupta et al. |
| 9,488,040 | B2 | 11/2016 | Chakrabarty et al. |
| 9,534,836 | B2 | 1/2017 | Dubettier-Grenier et al. |
| 9,725,644 | B2 | 8/2017 | Babcock et al. |
| 2005/0189112 | A1 | 9/2005 | Taylor et al. |
| 2006/0243437 | A1 | 11/2006 | Albers et al. |
| 2006/0289166 | A1 | 12/2006 | Stromquist et al. |
| 2007/0000666 | A1 | 1/2007 | Vozniak et al. |
| 2007/0187340 | A1 | 8/2007 | Oresti et al. |
| 2008/0087041 | A1 | 4/2008 | Denton et al. |
| 2010/0032171 | A1 | 2/2010 | Bali et al. |
| 2012/0000660 | A1 | 1/2012 | Gatlin et al. |
| 2012/0037370 | A1 | 2/2012 | Johnson |
| 2012/0047942 | A1 | 3/2012 | Kolodziej |
| 2013/0168086 | A1 | 7/2013 | Roberts |
| 2013/0199774 | A1 | 8/2013 | Sultenfuss et al. |
| 2013/0213085 | A1 | 8/2013 | Ward |
| 2013/0220605 | A1 | 8/2013 | Vandor |
| 2013/0228330 | A1 | 9/2013 | Loree et al. |
| 2013/0299167 | A1 | 11/2013 | Fordyce et al. |
| 2014/0000899 | A1 | 1/2014 | Nevison |
| 2014/0124208 | A1 | 5/2014 | Loree et al. |
| 2014/0174747 | A1 | 6/2014 | Kelly et al. |
| 2014/0366577 | A1 | 12/2014 | Zubrin et al. |
| 2015/0021022 | A1 | 1/2015 | Ladva et al. |
| 2015/0060075 | A1 | 3/2015 | Blom et al. |
| 2015/0152318 | A1 | 6/2015 | Travis |
| 2015/0167550 | A1 | 6/2015 | Vandervort et al. |
| 2015/0184932 | A1 | 7/2015 | Higginbotham et al. |
| 2015/0233222 | A1 | 8/2015 | Teklu et al. |
| 2015/0368566 | A1 | 12/2015 | Young et al. |
| 2016/0069171 | A1 | 3/2016 | Stancliffe et al. |
| 2016/0122628 | A1 | 5/2016 | Babcock et al. |
| 2016/0238313 | A1 | 8/2016 | Shotts |
| 2016/0280607 | A1 | 9/2016 | Land et al. |
| 2017/0044425 | A1 | 2/2017 | Barati Ghahfarokhi |
| 2017/0114269 | A1 | 4/2017 | Hancu et al. |
| 2017/0218742 | A1 | 8/2017 | Babcock et al. |
| 2017/0218743 | A1 | 8/2017 | Babcock et al. |
| 2017/0275520 | A1 | 9/2017 | Babcock et al. |
| 2017/0275521 | A1 | 9/2017 | Babcock et al. |
| 2017/0275526 | A1 | 9/2017 | Babcock et al. |
| 2017/0292057 | A1 | 10/2017 | Babcock et al. |
| 2017/0292059 | A1 | 10/2017 | Babcock et al. |
| 2017/0292354 | A1 | 10/2017 | Babcock et al. |
| 2017/0298268 | A1 | 10/2017 | Babcock et al. |

FOREIGN PATENT DOCUMENTS

| | | |
|---|---|---|
| FR | 2466606 A1 | 4/1981 |
| GB | 2219818 A | 12/1989 |
| WO | 8912158 A1 | 12/1989 |
| WO | 98/04807 A1 | 2/1998 |
| WO | 2010025540 A1 | 3/2010 |
| WO | 2012097424 A1 | 7/2012 |
| WO | 2015020654 A1 | 2/2015 |
| WO | 2015030908 A2 | 3/2015 |
| WO | 2016064645 A1 | 4/2016 |

OTHER PUBLICATIONS

Ginley, "Osudo Reservoir Fluid Study Jordan B No. 1 Well", http://ocdimage.emnrd.state.nm.us/imaging/filestore/SantaFeAdmin/CF/ADA-03-00539 Case Files Part 6/10796_ 4159.pdf, pp. 1,5; table 2, Jan. 1, 1992.

Holtz et al., "Summary Integrated Geologic and Engineering Determination of Oil- Reserve-Growth Potential in Carbonate Reservoirs", https://www.onepetro.org/download/journal-paper/SPE-22900-PA?id=journal-paper/SPE-22900-PA, p. 1250 and 1253, Jan. 1, 1992.

International Invitation to Pay Additional Fees dated Feb. 13, 2017, corresponding to Application No. PCT/US2016/063132.

International Invitation to Pay Additional Fees dated Apr. 10, 2017, corresponding to Application No. PCT/US2017/012561.

International Search Report and Written Opinion dated Jan. 8, 2016, corresponding to Application No. PCT/US2015/055627.

International Search Report and Written Opinion dated Feb. 7, 2017, corresponding to Application No. PCT/US2016/063140.

International Search Report and Written Opinion dated Feb. 7, 2017, corresponding to Application No. PCT/US2016/063148.

International Search Report and Written Opinion dated Mar. 29, 2017, corresponding to Application No. PCT/US2016/067454.

International Search Report and Written Opinion dated Mar. 30, 2017, corresponding to Application No. PCT/US2016/067458.

International Search Report and Written Opinion dated Apr. 4, 2017, corresponding to Application No. PCT/US2017/012566.

International Search Report and Written Opinion dated May 10, 2017, corresponding to Application No. PCT/US2016/063127.

International Search Report and Written Opinino dated May 10, 2017, corresponding to Application No. PCT/US2016/063132.

International Search Report and Written Opinion dated Jun. 7, 2017, corresponding to Application No. PCT/US2017/012561.

International Search Report and Written Opinion dated Sep. 21, 2017, corresponding to Application No. PCT/US2017/014696.

International Search Report and Written Opinion dated Nov. 7, 2017, corresponding to Application No. PCT/US2017/019619.

M. Asadi et al., "Water-Free Fracturing: A Case History", Society of Petroleum Engineers, SPE-175988-MS, 14 Pages.

Nakashima et al., "SPE-177801-MS Development of a Giant Carbonate Oil Field, Part 2: Mitigation from Pressure Maintenance Developement to Sweep Oriented IOR Development", https://Iwww.onepetro.org/download/conference--aper/SPE-177801-MS?id=conference-paper/SPE-177801-MS, pp. 1-8 and 12-16, Jan. 1, 2015.

Pazuki et al., "A modified Flory-Huggins model for prediction of asphaltenes precipitation in crude oil", Fuel, IPC Science and Technology Press, Guildford, GB, vol. 85, No. 7-8, pp. 1083-1086, May 1, 2016.

Qing Sun et al., "Quantification of uncertainty in recovery efficiency predictions: lessons learned from 250 mature carbonate fields", SPE 84459, pp. 1-15, Jan. 1, 2005.

S.Rassenfoss; "In Search of the Waterless Fracture", JPT, Jun. 30, 2013, pp. 46-54, XP055237780.

International Search Report and Written Opinion dated Sep. 4, 2018, corresponding to Application No. PCT/US2018/042929.

McGuire et al., "Ethane-Based Enhanced Oil Rocovery: An Innovative and Profitable Enhanced-Oil-Recovery Opportunity for a Low-Price Environment," Feb. 2017 SPE Reservoir Evaluation & Engineering, pp. 42-58.

SYSTEMS AND METHODS OF OPTIMIZING Y-GRADE NGL ENHANCED OIL RECOVERY FLUIDS

FIELD

Embodiments of the disclosure relate to systems and methods for enhanced and/or improved oil recovery using Y-Grade NGL.

BACKGROUND

Estimates of worldwide oil in-place range up to 1.5 trillion barrels. Using that figure, since conventional recovery methods (primary and secondary) typically extract one-third of the original oil-in-place in a reservoir, it is estimated that the oil remaining as residual oil saturation after conventional recovery would be approximately 1.0 trillion barrels. Several enhanced oil recovery (EOR) techniques generally grouped together as tertiary production schemes have targeted this resource. In the past, chemical, thermal, and miscible techniques have been used by the industry. These EOR techniques typically involve injection of chemical compounds dissolved in water, the injection of steam, or the injection of a gas that is miscible with the oil in place.

The choice of EOR technique to be used is also dependent on other considerations such as depth, temperature, and amount of oil remaining in place. Much of the design phase of an EOR project is spent in the search for the combination of processes and injection schemes that will maximize oil recovery relative to the cost of implementing a particular technique. Most injection materials in use today have properties that differ considerably from the hydrocarbons in the reservoirs. Such differences in properties can reduce extraction efficiency.

Therefore there is a need for new and improved enhanced and/or improved oil recovery techniques.

SUMMARY

A method of optimizing a Y-Grade NGL enhanced oil recovery fluid comprises gathering geostatic data and reservoir fluid data of a hydrocarbon bearing reservoir; assessing availability of a supply of Y-Grade NGL and a gas; using the reservoir fluid data and data regarding the composition of the Y-Grade NGL and the gas to determine an equation of state; generating a hydrocarbon foam through a foam generation module, wherein the foam generation module includes customizing a surfactant to be mixed with the Y-Grade NGL and the gas to form the hydrocarbon foam, adjusting foam stability of the hydrocarbon foam, customizing the hydrocarbon foam, and determining a foam rheology of the hydrocarbon foam; formulating computational algorithms for the equation of state and the foam rheology; formulating a 3-D compositional reservoir simulation model as represented by the geostatic data, previously matched historical production and pressure data, and the computational algorithms to simulate an enhanced and/or improved oil recovery process of the reservoir using the hydrocarbon foam; and running multiple simulations for different hydrocarbon foams generated by the foam generation module to determine which hydrocarbon foam will obtain an optimum fluid recovery.

A method of optimizing a Y-Grade NGL enhanced oil recovery fluid comprises gathering geostatic data and reservoir fluid data of a hydrocarbon bearing reservoir; assessing availability of a supply of Y-Grade NGL, a gas, and water; using the reservoir fluid data and data regarding the composition of the Y-Grade NGL, the gas, and the water to determine an equation of state; generating an emulsion based foam through an emulsion based foam generation module, wherein the emulsion based foam generation module includes customizing a surfactant to be mixed with the Y-Grade NGL, the gas, and the water to form the emulsion based foam, adjusting foam stability of the emulsion based foam, customizing the emulsion based foam, and determining an emulsion based foam rheology of the emulsion based foam; formulating computational algorithms for the equation of state and the emulsion based foam rheology; formulating a 3-D compositional reservoir simulation model as represented by the geostatic data, previously matched historical production and pressure data, and the computational algorithms to simulate an enhanced and/or improved oil recovery process of the reservoir using the emulsion based foam; and running multiple simulations for different emulsion based foams generated by the emulsion based foam generation module to determine which emulsion based foam will obtain an optimum fluid recovery.

A method of optimizing a Y-Grade NGL enhanced oil recovery fluid comprises gathering geostatic data and reservoir fluid data of a hydrocarbon bearing reservoir; assessing availability of a supply of Y-Grade NGL and water; using the reservoir fluid data and data regarding the composition of the Y-Grade NGL and the water to determine an equation of state; generating an emulsion through an emulsion generation module, wherein the emulsion generation module includes customizing a surfactant to be mixed with the Y-Grade NGL and the water to form the emulsion, adjusting stability of the emulsion, customizing the emulsion, and determining a rheology of the emulsion; formulating computational algorithms for the equation of state and the emulsion rheology; formulating a 3-D compositional reservoir simulation model as represented by the geostatic data, previously matched historical production and pressure data, and the computational algorithms to simulate an enhanced and/or improved oil recovery process of the reservoir using the emulsion; and running multiple simulations for different emulsions generated by the emulsion generation module to determine which emulsion will obtain an optimum fluid recovery.

A method of optimizing a Y-Grade NGL enhanced oil recovery fluid comprises gathering geostatic data and reservoir fluid data of a hydrocarbon bearing reservoir; assessing availability of a supply of Y-Grade NGL; using the reservoir fluid data and data regarding the composition of the Y-Grade NGL to determine an equation of state; generating a gelled enhanced oil recovery fluid through a gel generation module, wherein the gel generation module includes customizing a gelling agent to be mixed with the Y-Grade NGL to form the gelled enhanced oil recovery fluid, adjusting gel stability of the gelled enhanced oil recovery fluid, customizing the gelled enhanced oil recovery fluid, and determining a gel rheology of the gelled enhanced oil recovery fluid; formulating computational algorithms for the equation of state and the gel rheology; formulating a 3-D compositional reservoir simulation model as represented by the geostatic data, previously matched historical production and pressure data, and the computational algorithms to simulate an enhanced and/or improved oil recovery process of the reservoir using the gelled enhanced oil recovery fluid; and running multiple simulations for different gelled enhanced oil recovery fluids generated by the gel generation module to determine which gelled enhanced oil recovery fluid will obtain an optimum fluid recovery.

DETAILED DESCRIPTION

Embodiments of the disclosure include enhanced oil recovery fluids used for the enhanced and/or improved oil recovery of residual hydrocarbons from hydrocarbon bearing reservoirs. The enhanced oil recovery fluids comprise naturally occurring, locally available components as a cost effective approach. The enhanced oil recovery fluids help reduce and/or eliminate interfacial tension of the residual hydrocarbons to enhance and/or improve oil recovery.

In one embodiment, the enhanced oil recovery fluids comprise Y-Grade natural gas liquids (referred to herein as Y-Grade NGL). Sweep efficiencies can be improved if Y-Grade NGL is injected into the reservoir in small volumes (also referred to as "slugs") that are alternated with slugs of a mobility control fluid, such as nitrogen, water, and/or viscosified water, as a means of improving the mobility of the injected fluids. Y-Grade NGL is a low cost miscible solvent that is an excellent candidate for enhanced and/or improved hydrocarbon recovery.

Y-Grade NGL is an un-fractionated hydrocarbon mixture comprising ethane, propane, butane, isobutane, and pentane plus. Pentane plus comprises pentane, isopentane, and/or heavier weight hydrocarbons, for example hydrocarbon compounds containing at least one of C5 through C8+. Pentane plus may include natural gasoline for example.

Typically, Y-Grade NGL is a by-product of condensed and de-methanized hydrocarbon streams that are produced from shale wells for example and transported to a centralized facility. Y-Grade NGL can be locally sourced from a splitter facility, a natural gas plant, and/or a refinery and transported by tanker truck or pipeline to a point of use. In its un-fractionated or natural state, Y-Grade NGL has no dedicated market or known use. Y-Grade NGL must undergo processing known as fractionation to create discrete components before its true value is proven.

The Y-Grade NGL composition can be customized for handling as a liquid under various conditions. Since the ethane content of Y-Grade NGL affects the vapor pressure, the ethane content can be adjusted as necessary. According to one example, Y-Grade NGL may be processed to have a low ethane content, such as an ethane content within a range of 3-12 percent by volume, to allow the Y-Grade NGL to be transported as a liquid in low pressure storage vessels. According to another example, Y-Grade NGL may be processed to have a high ethane content, such as an ethane content within a range of 38-60 percent by volume, to allow the Y-Grade NGL to be transported as a liquid in high pressure pipelines.

Y-Grade NGL differs from liquefied petroleum gas ("LPG"). One difference is that LPG is a fractionated product comprised of primarily propane, or a mixture of fractionated products comprised of propane and butane. Another difference is that LPG is a fractioned hydrocarbon mixture, whereas Y-Grade NGL is an unfractionated hydrocarbon mixture. Another difference is that LPG is produced in a fractionation facility via a fractionation train, whereas Y-Grade NGL can be obtained from a splitter facility, a natural gas plant, and/or a refinery. A further difference is that LPG is a pure product with the exact same composition, whereas Y-Grade NGL can have a variable composition.

In its unfractionated state, Y-Grade NGL is not an NGL purity product and is not a mixture formed by combining one or more NGL purity products. An NGL purity product is defined as an NGL stream having at least 90% of one type of carbon molecule. The five recognized NGL purity products are ethane (C2), propane (C3), normal butane (NC4), isobutane (IC4) and natural gasoline (C5+). The unfractionated hydrocarbon mixture is sent to a fractionation facility, where it is cryogenically cooled and passed through a fractionation train that consists of a series of distillation towers, referred to as deethanizers, depropanizers, and debutanizers, to fractionate out NGL purity products from the unfractionated hydrocarbon mixture. Each distillation tower generates an NGL purity product. Liquefied petroleum gas is an NGL purity product comprising only propane, or a mixture of two or more NGL purity products, such as propane and butane. Liquefied petroleum gas is therefore a fractionated hydrocarbon or a fractionated hydrocarbon mixture.

In one embodiment, Y-Grade NGL comprises 30-80%, such as 40-60%, for example 43%, ethane; 15-45%, such as 20-35%, for example 27%, propane; 5-10%, for example 7%, normal butane; 5-40%, such as 10-25%, for example 10%, isobutane; and 5-25%, such as 10-20%, for example 13%, pentane plus. Methane is typically less than 1%, such as less than 0.5% by liquid volume.

In one embodiment, Y-Grade NGL comprises condensed, dehydrated, desulfurized, and de-methanized natural gas stream components that have a vapor pressure of not more than about 600 psig at 100 degrees Fahrenheit, with aromatics below about 1 weight percent, and olefins below about 1 percent by liquid volume. Materials and streams useful for the embodiments described herein typically include hydrocarbons with melting points below about 0 degrees Fahrenheit.

In one embodiment, Y-Grade NGL may be mixed with a chemical agent. The chemical agent may be mixed with a solubilizing fluid to liquefy any dry chemicals to aid in mixing with the Y-Grade NGL. The solubilizing fluid may comprise fractionated or refined hydrocarbons, such as C3, C4, C5, C6, C7, C8, C9, and mixtures thereof. The solubilizing fluid may comprise C3+ hydrocarbons, including propane, butane, pentane, naphtha, toluene, diesel, natural gasoline, and any combination thereof.

Figure 1:
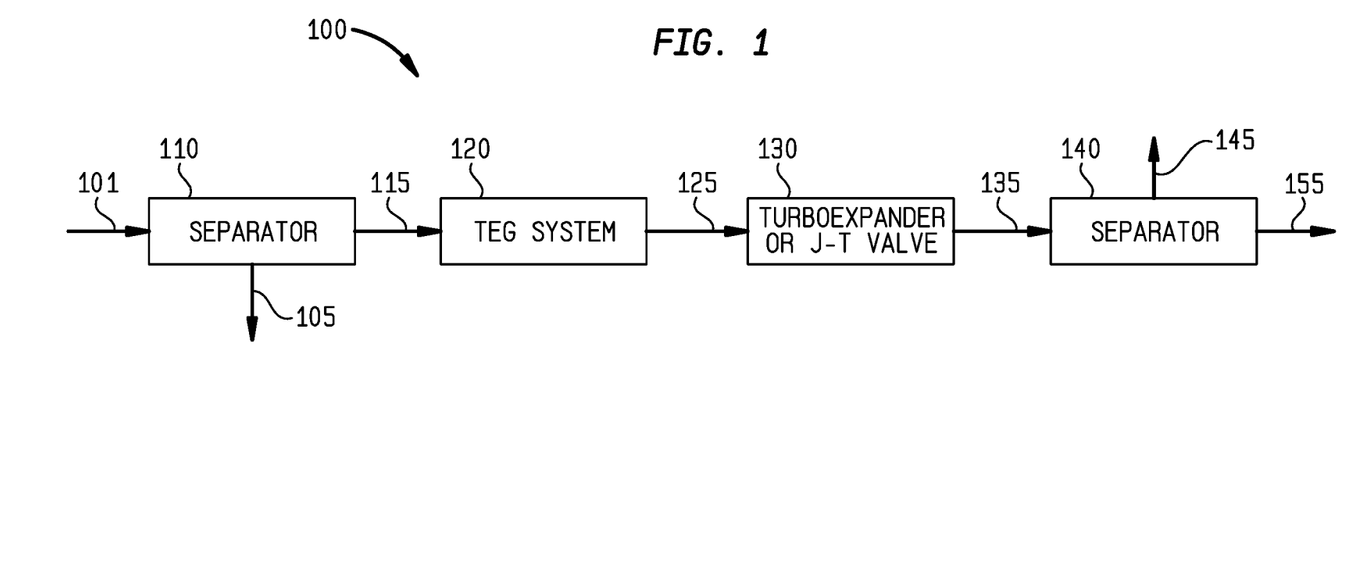
FIG. 1 is a schematic view of a system for obtaining Y-Grade NGL according to one embodiment.

FIG. 1 is a schematic view of a Y-Grade NGL system 100 for obtaining Y-Grade NGL, according to one embodiment, for use with embodiments described herein. The system 100 includes a first separator 110, a triethylene glycol ("TEG") system 120, a turboexpander 130 (or alternatively a Joule-Thompson valve), and a second separator 140. A hydrocarbon stream 101, such as a wet natural gas stream, flows into the first separator 110 where it is separated into a liquid stream 105 and a gas stream 115. The liquid stream 105 comprises liquid hydrocarbons and water. The gas stream 115 flows into the TEG system 120 where water vapor is removed to dehydrate the gas stream 115. The TEG system 120 dehydrates the gas stream 115 that is discharged from the first separator 110 to a water dew point up to −100 degrees Fahrenheit. The gas stream 125 exiting the TEG system 120 flows into the turboexpander 130 (or alternatively the Joule-Thompson valve), which cools the gas stream 125 to a temperature at or below 0 degrees Fahrenheit, for example to a temperature between 0 degrees Fahrenheit and −100 degrees Fahrenheit, for example about −30 degrees Fahrenheit.

The gas stream 125 is cooled to a temperature at or below 0 degrees Fahrenheit to condense out Y-Grade NGL from the remaining gas stream, which is primarily methane. The cooled fluids 135 flow into the second separator 140 where the gas stream 145, which is primarily methane, is separated out from the Y-Grade NGL 155. As a result, the Y-Grade NGL 155 is a byproduct of the condensed and de-methanized hydrocarbon stream 101.

In one embodiment, the gas stream 145 may also comprise ethane in an amount of about 1 percent to about 50 percent by volume. The amount of ethane separated out with the methane can be controlled by the pressure maintained in the second separator 140. The pressure in the second separator 140 may be about 600 psi or less. As the pressure is lowered in the second separator 140, the ethane content of the gas stream 145 is increased, and the ethane content of the Y-Grade NGL 155 is decreased. The Y-Grade NGL 155 may be used to form any of the enhanced oil recovery fluids and/or with any of the systems and methods described herein.

According to one example, Y-Grade NGL comprises about 43% ethane, about 27% propane, about 7% normal butane, about 10% isobutane, and about 13% pentane plus at a maximum vapor pressure of about 600 psig at 100 degrees Fahrenheit per American Society for Testing and Materials (ASTM) according to the standard testing procedure D-6378 with methane, aromatics, and olefin maximums of 0.5% L.V. % per GPA 2177, 1.0 wt % of total stream per GPA 2186 and 1.0 L.V. % per GPA 2186, respectively.

According to one example, Y-Grade NGL comprises about 28% ethane, about 42% propane, about 13% normal butane, about 7% isobutane, and about 10% pentane plus. According to one example, Y-Grade NGL comprises about 48% ethane, about 31% propane, about 9% normal butane, about 5% isobutane, and about 7% pentane plus. According to one example, Y-Grade NGL comprises about 37%-43% ethane, about 22%-23% propane, about 7% normal butane, about 9%-11 isobutane, and about 13%-16% pentane plus. According to one example, Y-Grade NGL comprises about 10%-20% of at least one hydrocarbon compound having five carbon elements ($C_5$) or more.

Y-Grade NGL may comprise one or more combinations, as a whole or in part, of the Y-Grade NGL examples and/or embodiments described herein.

Figure 2:
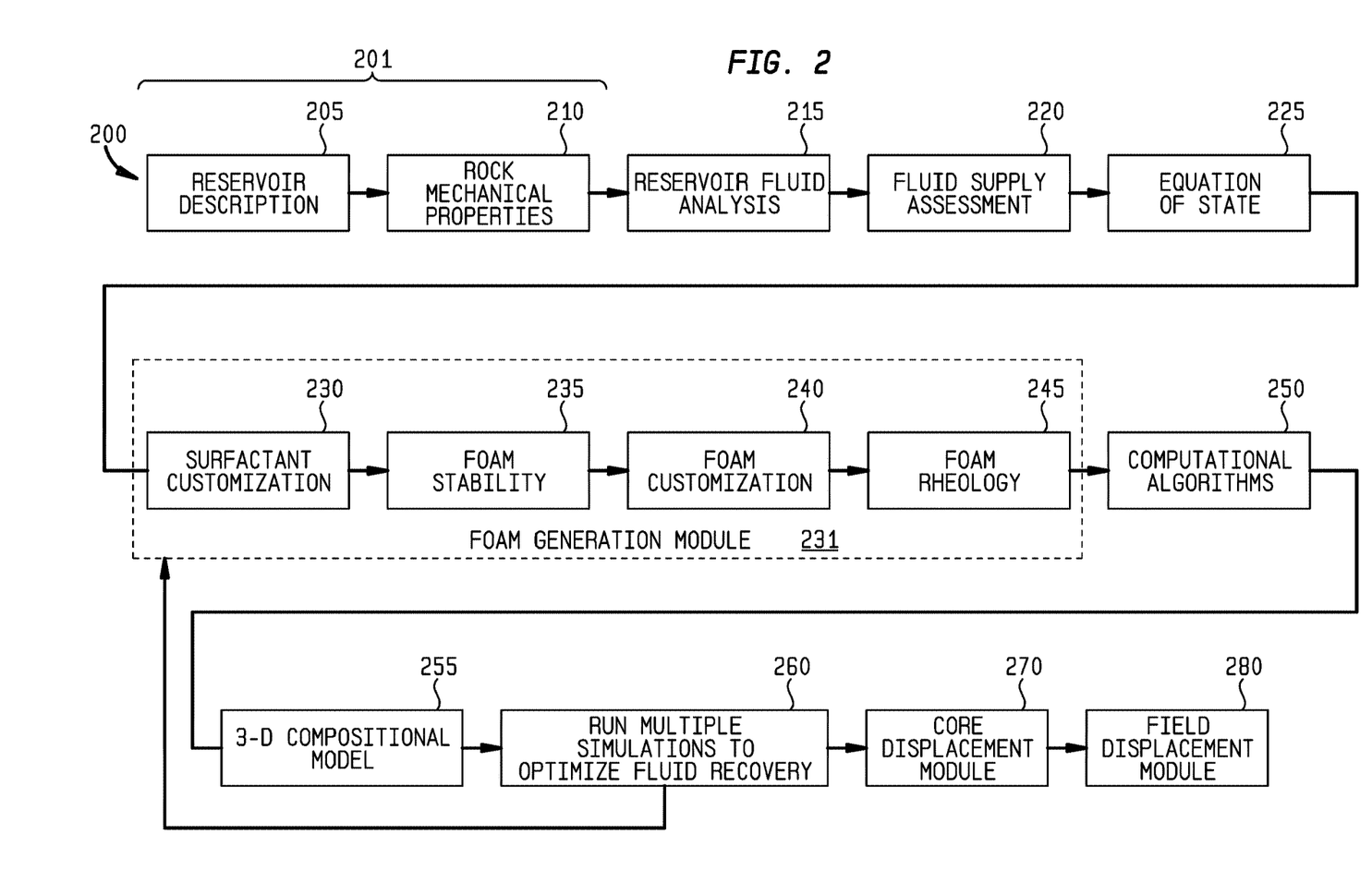
FIG. 2 is a schematic view of a method for optimizing hydrocarbon foam based Y-Grade NGL enhanced oil recovery fluids according to one embodiment.

FIG. 2 is a schematic view of a method 200 for optimizing hydrocarbon foam based Y-Grade NGL enhanced oil recovery fluids according to one embodiment.

The method 200 includes a step of gathering geostatic data 201 of a subsurface formation, such as a hydrocarbon bearing reservoir. Gathering the geostatic data 201 includes obtaining a description of the reservoir 205, including but not limited to data regarding porosity, permeability, fluid saturations, well location, thickness, depth, pressures, historical production and pressures, and/or temperatures of the reservoir. Gathering geostatic data 201 also includes conducting an analysis of the rock mechanical properties 210, including but not limited to data regarding Young's-modulus of elasticity and/or Poisson's ratio of the rock in the reservoir. The method 200 further includes a step of conducting a reservoir fluid analysis 215 to gather data regarding the reservoir fluid properties, including but not limited to composition, viscosity, density, gas/oil ratio, and/or water/oil ratio of the fluids in the reservoir.

The method 200 further includes a step of assessing the availability of a supply of fluids 220 needed to create the hydrocarbon foam based Y-Grade NGL enhanced oil recovery fluids. To create hydrocarbon foam, the supply of fluids 220 will comprise Y-Grade NGL and a gas. The gas that can be used to form the hydrocarbon foam may comprise at least one of nitrogen, carbon dioxide, natural gas, methane, LNG, and ethane. An assessment is made to determine the quantity and/or composition of the Y-Grade NGL and/or the gas that is available for forming the hydrocarbon foam based Y-Grade NGL enhanced oil recovery fluids.

The method 200 further includes a step of determining an equation of state 225 based on the reservoir fluid analysis 215 and the assessment of the supply of fluids 220. The equation of state 225 may be based on the reservoir fluid data and the quantity and/or composition of the Y-Grade NGL and/or the gas.

The method 200 further includes a step of generating a hydrocarbon foam through a foam generation module 231. The foam generation module includes a step of customizing a surfactant 230 to be mixed with the Y-Grade NGL and the gas to form the hydrocarbon foam, a step of adjusting foam stability 235 of the hydrocarbon foam, a step of customizing the hydrocarbon foam 240, and a step of determining a foam rheology 245 of the hydrocarbon foam.

The step of customizing the surfactant 230 may include selecting a surfactant that is preferentially or selectively soluble in light hydrocarbons. Customizing the surfactant 230 may also include adjusting the molecular weight of the surfactant. Customizing the surfactant 230 may also include selecting at least one of a siloxane surfactant, a fluorosurfactant, a fatty acid ester, a glyceride, a silicon emulsifier, and a hydrophobic silica powder as the surfactant. The surfactant 230 may also be customized by adjusting the concentration of surfactant by up to 5% by weight of the liquid phase of the hydrocarbon foam.

The step of customizing the surfactant 230 may also include selecting at least one of an anionic surfactant including The anionic surfactant comprises at least one of 2-Acrylamido-2-methylpropane sulfonic acid, ammonium lauryl sulfate, ammonium perfluorononanoate, docusate, magnesium laureth sulfate, MBAS assay, perfluorobutanesulfonic acid, perfluorononanoic acid, perfluorooctanesulfonic acid, perfluorooctanoic acid, phospholipid, potassium lauryl sulfate, soap, soap substitute, sodium alkyl sulfate, sodium dodecyl sulfate, sodium dodecylbenzenesulfonate, sodium laurate, sodium laureth sulfate, sodium lauroyl sarcosinate, sodium myreth sulfate, sodium nonanoyloxybenzenesulfonate, sodium pareth sulfate, sodium stearate, and sulfolipid.

The step of adjusting foam stability 235 includes several ways of adjusting the stability of the foam. The stability of the foam may be adjusted by adjusting foam quality based on the amount of gas, such as nitrogen, that is used to form the hydrocarbon foam. The stability of the foam may be adjusted by adding nanoparticles to reduce fluid loss of the liquid phase of the hydrocarbon foam. The stability of the foam may be adjusted by adding a hydrocarbon soluble co-polymer to viscosify the liquid phase of the hydrocarbon foam. The stability of the foam may be adjusted by changing the type of gas used to form the hydrocarbon foam.

The step of adjusting foam stability 235 may also include adjusting the apparent viscosity of the foam. The apparent viscosity of the foam may be adjusted by adjusting foam quality based on the amount of gas, such as nitrogen, that is used to form the hydrocarbon foam. The apparent viscosity of the foam may be adjusted by adding a hydrocarbon soluble co-polymer to viscosify the liquid phase of the hydrocarbon foam. The apparent viscosity of the foam may be adjusted by adding a secondary fluid comprising up to 10% of the liquid phase of the hydrocarbon foam. The secondary fluid may comprise at least one of aromatics, alkanes, and crude oil.

The step of customizing the foam 240 includes adding a secondary fluid to the hydrocarbon foam, such as to control the mobility of the hydrocarbon foam in the reservoir. The secondary fluid may comprise at least one of aromatics, alkanes, and crude oil. Aromatics may comprise at least one of benzene, naphtha, xylene, toluene, fuel oils, olefins, and diesel. Alkanes may comprise at least one of heptane, octane, and hexane. Crude oil may comprise at least one of NGL's, condensate, light oil, medium oil, and reservoir oil.

The step of determining foam rheology 245 includes determining the rheology of the hydrocarbon foam. The foam rheology 245 may be defined by, including but not limited to, its apparent viscosity, density, wettability, relative permeability of the hydrocarbon foam, and saturation of the hydrocarbon foam as a function of temperature, pressure, and composition of the hydrocarbon foam.

After the hydrocarbon foam is generated by the foam generation module 231 and the foam rheology 245 is determined, the method 200 further includes a step of formulating computational algorithms 250 for the equation of state 225 and the foam rheology 245. The method 200 further includes a step of formulating a 3-D compositional reservoir simulation model 255. The 3-D compositional reservoir simulation model 255 is formulated by incorporating the geostatic data 201, calibrating the 3-D compositional reservoir simulation model 255 by history matching with historical production and pressure data, and modifying the 3-D compositional reservoir simulation model 255 by incorporating the computational algorithms 250 to simulate an enhanced and/or improved oil recovery process of the reservoir using the hydrocarbon foam. The simulation will provide data regarding how the hydrocarbon foam is transported to the reservoir and how the hydrocarbon foam stimulates the reservoir.

After the simulation is run in the 3-D compositional reservoir simulation model 255, the method 200 further includes a step of running multiple simulations 260 by generating different types of hydrocarbon foams using the foam generation module to gather enough data from the simulations to determine which hydrocarbon foam will achieve an optimum hydrocarbon recovery in the reservoir.

The method 200 also includes a core displacement module 270. In the core displacement module 270, one or more core displacement tests are run on one or more representative reservoir cores that are adjusted to residual oil conditions at reservoir temperature and pressure and simulate actual post water flooding conditions. Residual oil in each representative reservoir core is then displaced at reservoir pressure and temperature conditions with one or more of the hydrocarbon foams to evaluate the displacement efficiency of the hydrocarbon foams. Additional representative reservoir cores can also be displaced with carbon dioxide and other enhanced and/or improved oil recovery fluids for comparison with the representative reservoir cores that are displaced with the hydrocarbon foams to determine which one provides the optimum fluid displacement.

The method 200 also includes a field displacement module 280. In the field displacement module 280, one or more field displacement tests are run to demonstrate the enhanced and/or improved oil recovery displacement efficiency of one or more of the hydrocarbon foams along with associated costs under actual reservoir conditions. A field displacement test utilizes two or more wells wherein at least one well is an injection well and one well is a production well. The injection and production wells may either currently exist or are specifically drilled and completed in the reservoir of interest typically on close spacing to reduce response time and fluid costs. A volume (e.g. 30%-50% pore volume) of hydrocarbon foam is injected under reservoir conditions with a specified injection protocol through the injection well and then displaced with a volume (e.g. 50%-70% pore volume) of a final displacement fluid, which may include carbon dioxide, nitrogen, natural gas, methane, LNG, ethane, water, viscosified water, formation water, and/or combinations thereof. The fluids, including formation oil, are displaced and produced back to the surface via the production well.

Figure 3:
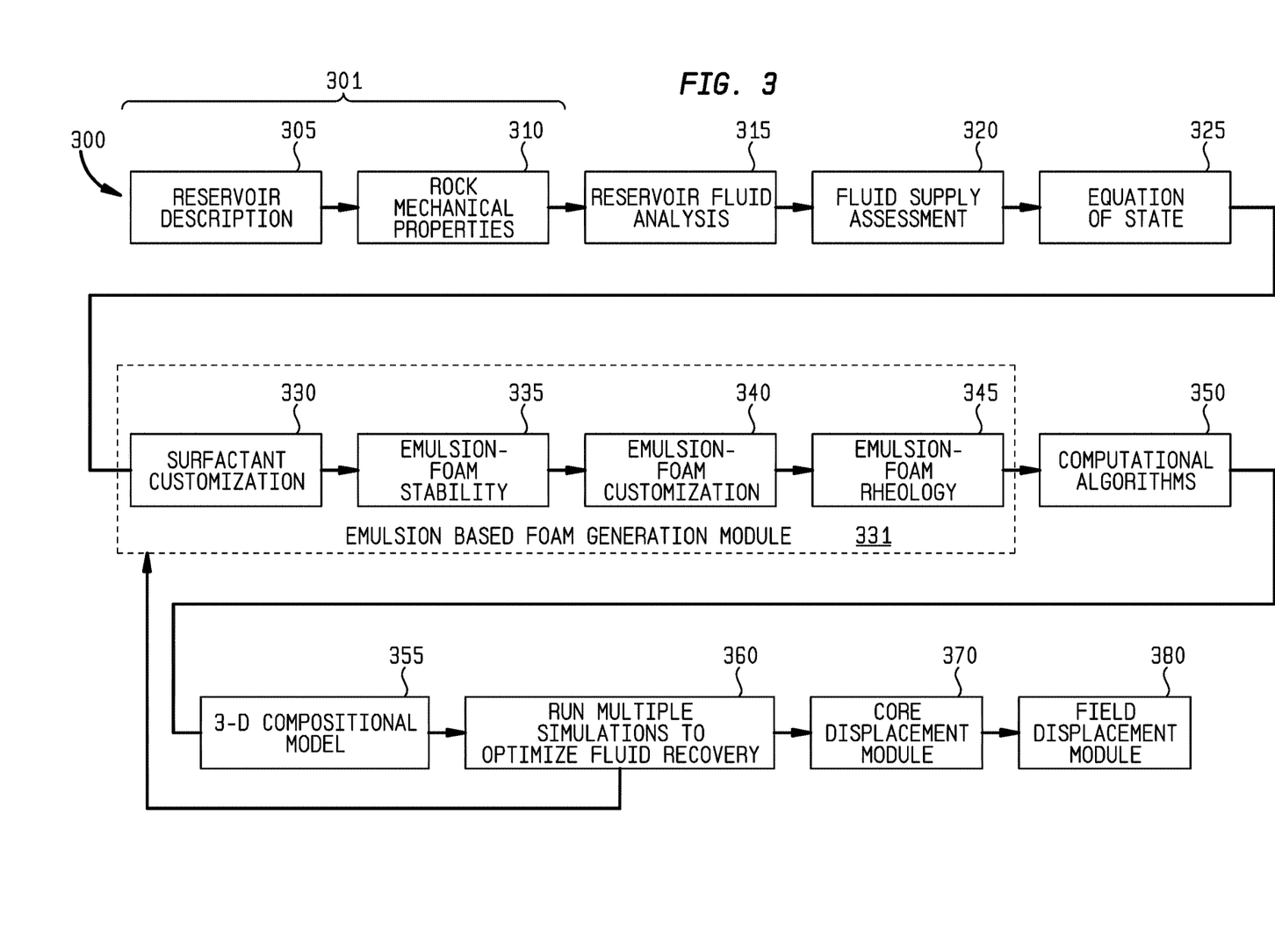
FIG. 3 is a schematic view of a method for optimizing emulsion foam based Y-Grade NGL enhanced oil recovery fluids according to one embodiment.

FIG. 3 is a schematic view of a method 300 for optimizing emulsion based foam Y-Grade NGL enhanced oil recovery fluids according to one embodiment.

The method 300 includes the steps of gathering geostatic data 301 of a subsurface formation, such as a hydrocarbon bearing reservoir, and conducting a reservoir fluid analysis 315 to gather data regarding the reservoir fluid properties, similar to the steps of gathering geostatic data 201 and conducting a reservoir fluid analysis 215 in the method 200.

The method 300 further includes a step of assessing the availability of a supply of fluids 320 needed to create the emulsion based foam Y-Grade NGL enhanced oil recovery fluids. To create the emulsion based foam, the supply of fluids 320 will comprise Y-Grade NGL, a gas, such as nitrogen, and water. The gas that can be used to form the emulsion based foam may comprise at least one of nitrogen, carbon dioxide, natural gas, methane, LNG, and ethane. The water can be formation water, brine, seawater, or potassium chloride water, either of which comprises up to 10% of the liquid phase of the emulsion based foam. The potassium chloride water may comprise up to 4% potassium chloride. An assessment is made to determine the quantity and/or composition of the Y-Grade NGL, the gas, and/or the water that is available for forming the emulsion based foam Y-Grade NGL enhanced oil recovery fluids.

The method 300 further includes a step of determining an equation of state 325 based on the reservoir fluid analysis 315 and the assessment of the supply of fluids 320. The equation of state 325 may be based on the reservoir fluid data and the quantity and/or composition of the Y-Grade NGL, the gas, and/or the water.

The method 300 further includes a step of generating an emulsion based foam through an emulsion based foam generation module 331. The emulsion based foam generation module 331 includes one or more of the steps of customizing a surfactant 330 to be mixed with the Y-Grade NGL, the gas, and the water to form the emulsion based foam, adjusting emulsion based foam stability 335 of the emulsion based foam, customizing the emulsion based foam 340, and determining an emulsion based foam rheology 345 of the emulsion based foam.

The step of customizing the surfactant 330 may include selecting a surfactant that is preferentially or selectively soluble in light hydrocarbons, water, or both. For emulsion based foams, the surfactant 330 acts as a foaming agent, an emulsifying agent, or both. Customizing the surfactant 330 may also include adjusting the molecular weight of the surfactant. The surfactant 330 may also be customized by adjusting the concentration of surfactant by up to 5% by weight of the liquid phase of the emulsion based foam. Customizing the surfactant 330 comprises selecting at least one of a non-ionic surfactant, an anionic surfactant, and a cationic surfactant as the surfactant that is soluble in light hydrocarbons, water, or both.

The non-ionic surfactant comprises at least one of a siloxane, a fluorosurfactant, a fatty acid ester, a glyceride, a silicon emulsifier, and a hydrophobic silica powder.

The anionic surfactant comprises at least one of 2-Acrylamido-2-methylpropane sulfonic acid, ammonium lauryl sulfate, ammonium perfluorononanoate, docusate, magnesium laureth sulfate, MBAS assay, perfluorobutanesulfonic acid, perfluorononanoic acid, perfluorooctanesulfonic acid, perfluorooctanoic acid, phospholipid, potassium lauryl sulfate, soap, soap substitute, sodium alkyl sulfate, sodium dodecyl sulfate, sodium dodecylbenzenesulfonate, sodium laurate, sodium laureth sulfate, sodium lauroyl sarcosinate, sodium myreth sulfate, sodium nonanoyloxybenzenesulfonate, sodium pareth sulfate, sodium stearate, and sulfolipid.

The cationic surfactant comprises at least one of behentrimonium chloride, benzalkonium chloride, benzethonium chloride, bronidox, cetrimonium bromide, cetrimonium chloride, dimethyldioctadecylammonium bromide, dimethyldioctadecylammonium chloride, lauryl methyl gluceth-10 hydroxypropyl dimonium chloride, octenidine dihydrochloride, olaflur, N-Oleyl-1,3-propanediamine, stearalkonium chloride, tetramethylammonium hydroxide, and thonzonium bromide.

The step of adjusting emulsion based foam stability 335 includes several ways of adjusting the stability of the emulsion based foam. The stability of the emulsion based foam can be adjusted by adjusting foam quality based on the amount of gas, such as nitrogen, that is used to form the emulsion based foam. The stability of the emulsion based foam can be adjusted by adding nanoparticles to reduce fluid loss of the liquid phase of the emulsion based foam. The stability of the emulsion based foam can be adjusted by adding a hydrocarbon soluble co-polymer to viscosify the liquid phase of the emulsion based foam. The stability of the emulsion based foam can be adjusted by changing the type of gas used to form the emulsion based foam. The emulsion based foam stability may be adjusted by adding a water soluble co-polymer to viscosify the liquid phase of the emulsion based foam.

The step of adjusting emulsion based foam stability 335 may also include adjusting the apparent viscosity of the emulsion based foam. The apparent viscosity of the emulsion based foam may be adjusted by adjusting foam quality based on the amount of gas, such as nitrogen, that is used to form the emulsion based foam. The apparent viscosity of the foam may be adjusted by adding a hydrocarbon soluble co-polymer to viscosify the liquid phase of the emulsion based foam. The apparent viscosity of the emulsion based foam may be adjusted by adding a secondary fluid comprising up to 10% of the liquid phase of the emulsion based foam. The secondary fluid may comprise at least one of aromatics, alkanes, and crude oil. The apparent viscosity of the emulsion based foam may be adjusted by adding a water soluble co-polymer to viscosify the liquid phase of the emulsion based foam.

The step of customizing the emulsion based foam 340 includes adding a secondary fluid to the emulsion based foam. The secondary fluid may comprise at least one of aromatics, alkanes, and crude oil. Aromatics may comprise at least one of benzene, naphtha, xylene, toluene, fuel oils, olefins, and diesel. Alkanes may comprise at least one of heptane, octane, and hexane. Crude oil may comprise at least one of NGL's, condensate, light oil, medium oil, and reservoir oil.

The step of determining emulsion based foam rheology 345 includes determining the rheology of the emulsion based foam. The emulsion based foam rheology 345 may be defined by, including but not limited to, its apparent viscosity, density, wettability, relative permeability of the emulsion based foam, and saturation of the emulsion based foam as a function of temperature, pressure, and composition of the emulsion based foam.

After the emulsion based foam is generated by the emulsion based foam generation module 331 and the emulsion based foam rheology 345 is determined, the method 300 further includes a step of formulating computational algorithms 350 for the equation of state 325 and the emulsion based foam rheology 345. The method 300 further includes a step of formulating a 3-D compositional reservoir simulation model 355 as represented by the geostatic data 301 and the computational algorithms 350 to simulate an enhanced and/or improved oil recovery process of the reservoir using the emulsion based foam. The simulation will provide data regarding how the emulsion based foam is transported to the reservoir and how the emulsion based foam stimulates the reservoir.

After the simulation is run in the 3-D compositional reservoir simulation model 355, the method 300 further includes a step of running multiple simulations 360 by generating different types of emulsion based foams using the emulsion based foam generation module to gather enough data from the simulations to determine which emulsion based foam will achieve an optimum hydrocarbon recovery in the reservoir.

The method 300 also includes a core displacement module 370. In the core displacement module 370, one or more core displacement tests are run on one or more representative reservoir cores that are adjusted to residual oil conditions at reservoir temperature and pressure and simulate actual post water flooding conditions. Residual oil in each representative reservoir core is then displaced at reservoir pressure and temperature conditions with one or more of the emulsion based foams to evaluate the displacement efficiency of the emulsion based foams. Additional representative reservoir cores can also be displaced with carbon dioxide and other enhanced and/or improved oil recovery fluids for comparison with the representative reservoir cores that are displaced with the emulsion based foams to determine which one provides the optimum fluid displacement.

The method 300 also includes a field displacement module 380. In the field displacement module 380, one or more field displacement tests are run to demonstrate the enhanced and/or improved oil recovery displacement efficiency of one or more of the emulsion based foams along with associated costs under actual reservoir conditions. A field displacement test utilizes two or more wells wherein at least one well is an injection well and one well is a production well. The injection and production wells may either currently exist or are specifically drilled and completed in the reservoir of interest typically on close spacing to reduce response time and fluid costs. A volume (e.g. 30%-50% pore volume) of emulsion based foam is injected under reservoir conditions with a specified injection protocol through the injection well and then displaced with a volume (e.g. 50%-70% pore volume) of a final displacement fluid, which may include carbon dioxide, nitrogen, natural gas, methane, LNG, ethane, water, viscosified water, formation water, and/or combinations thereof. The fluids, including formation oil, are displaced and produced back to the surface via the production well.

Figure 4:
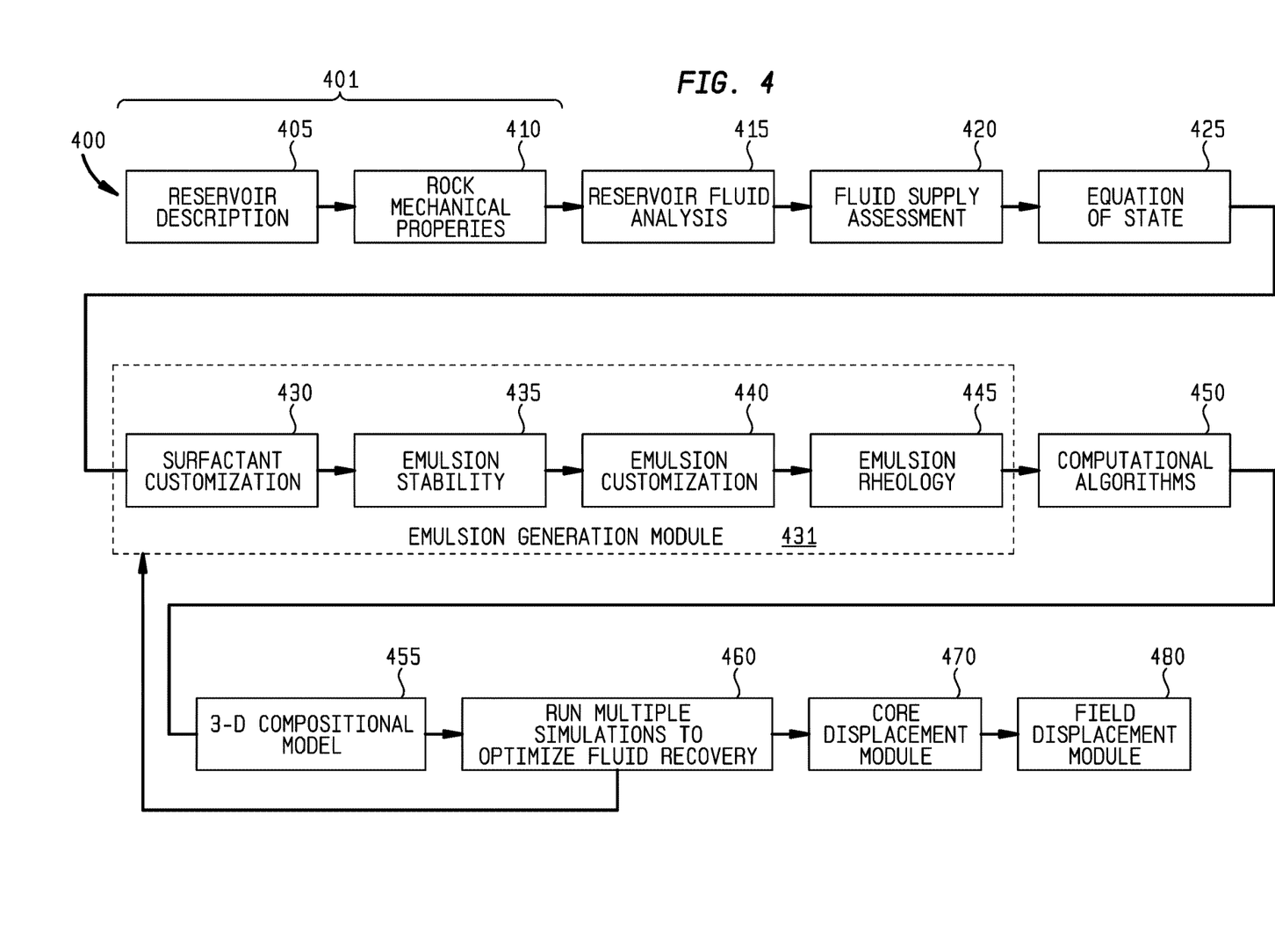
FIG. 4 is a schematic view of a method for optimizing emulsion based Y-Grade NGL enhanced oil recovery fluids according to one embodiment.

FIG. 4 is a schematic view of a method 400 for optimizing emulsion based Y-Grade NGL enhanced oil recovery fluids according to one embodiment.

The method 400 includes the steps of gathering geostatic data 401 of a subsurface formation, such as a hydrocarbon bearing reservoir, and conducting a reservoir fluid analysis 415 to gather data regarding the reservoir fluid properties, similar to the steps of gathering geostatic data 201 and conducting a reservoir fluid analysis 215 in the method 200.

The method 400 further includes a step of assessing the availability of a supply of fluids 420 needed to create the emulsion based Y-Grade NGL enhanced oil recovery fluids. To create an emulsion, the fluids 420 will comprise Y-Grade NGL and water. The water can be formation water, brine, seawater, or potassium chloride water, either of which comprises up to 10% of the liquid phase of the emulsion. The potassium chloride water may comprise up to 4% potassium chloride. An assessment is made to determine the quantity and/or composition of the Y-Grade NGL and/or the water that is available for forming the emulsion based Y-Grade NGL enhanced oil recovery fluids.

The method 400 further includes a step of determining an equation of state 425 based on the reservoir fluid analysis 415 and the assessment of the supply of fluids 420. The equation of state 425 may be based on the reservoir fluid data and the quantity and/or composition of the Y-Grade NGL and/or the water.

The method 400 further includes a step of generating an emulsion through an emulsion generation module 431. The emulsion generation module includes one or more of the steps of customizing a surfactant 430 to be mixed with the Y-Grade NGL and the water to form the emulsion, adjusting emulsion stability 435 of the emulsion, customizing the emulsion 440, and determining an emulsion rheology 445 of the emulsion.

The step of customizing the surfactant 430 may include selecting a surfactant that is preferentially or selectively soluble in light hydrocarbons, water, or both. For emulsions, the surfactant 430 acts as an emulsifying agent. Customizing the surfactant 430 may also include adjusting the molecular weight of the surfactant. The surfactant 430 may also be customized by adjusting the concentration of surfactant by up to 5% by weight of the emulsion. Customizing the surfactant 430 may also include selecting at least one of a non-ionic surfactant, an anionic surfactant, and a cationic surfactant as the surfactant that is soluble in light hydrocarbons, water, or both.

The non-ionic surfactant comprises at least one of a siloxane, a fluorosurfactant, a fatty acid ester, a glyceride, a silicon emulsifier, and a hydrophobic silica powder.

The anionic surfactant comprises at least one of 2-Acrylamido-2-methylpropane sulfonic acid, ammonium lauryl sulfate, ammonium perfluorononanoate, docusate, magnesium laureth sulfate, MBAS assay, perfluorobutanesulfonic acid, perfluorononanoic acid, perfluorooctanesulfonic acid, perfluorooctanoic acid, phospholipid, potassium lauryl sulfate, soap, soap substitute, sodium alkyl sulfate, sodium dodecyl sulfate, sodium dodecylbenzenesulfonate, sodium laurate, sodium laureth sulfate, sodium lauroyl sarcosinate, sodium myreth sulfate, sodium nonanoyloxybenzenesulfonate, sodium pareth sulfate, sodium stearate, and sulfolipid.

The cationic surfactant comprises at least one of behentrimonium chloride, benzalkonium chloride, benzethonium chloride, bronidox, cetrimonium bromide, cetrimonium chloride, dimethyldioctadecylammonium bromide, dimethyldioctadecylammonium chloride, lauryl methyl gluceth-10 hydroxypropyl dimonium chloride, octenidine dihydrochloride, olaflur, N-Oleyl-1,3-propanediamine, stearalkonium chloride, tetramethylammonium hydroxide, and thonzonium bromide.

The step of adjusting emulsion stability 435 includes several ways of adjusting the stability of the emulsion. The stability of the emulsion may be adjusted by changing the percent volume of water used to form the emulsion. The stability of the emulsion may be adjusted by adding a viscosifier to the emulsion. The viscosifier may comprise at least one of a hydrocarbon soluble co-polymer and a water soluble viscosifier. The water soluble viscosifer may comprise at least one of water soluble co-polymers, polysaccarides, guar gum, viscoelastic surfactants, crosslinkers, cellulosic viscosifiers, and hydroxyethyl cellulose.

The step of adjusting emulsion stability 435 may also include adjusting the apparent viscosity of the emulsion. The apparent viscosity of the emulsion may be adjusted by adding a hydrocarbon soluble or water soluble co-polymer to viscosify the liquid phase of the emulsion. The apparent viscosity of the emulsion may be adjusted by changing the percent volume of water used to form the emulsion. The apparent viscosity of the emulsion may be adjusted by adding a secondary fluid comprising up to 10% of the liquid phase of the emulsion. The secondary fluid may comprise at least one of aromatics, alkanes, and crude oil.

The step of customizing the emulsion 440 includes adding a secondary fluid to the emulsion. The secondary fluid may comprise at least one of aromatics, alkanes, and crude oil. Aromatics may comprise at least one of benzene, naphtha, xylene, toluene, fuel oils, olefins, and diesel. Alkanes may comprise at least one of heptane, octane, and hexane. Crude oil may comprise at least one of NGL's, condensate, light oil, medium oil, and reservoir oil.

The step of determining emulsion rheology 445 includes determining the rheology of the emulsion. The emulsion rheology 445 may be defined by, including but not limited to, its apparent viscosity, density, wettability, relative permeability of the emulsion, and saturation of the emulsion as a function of temperature, pressure, and composition of the emulsion.

After the emulsion is generated by the emulsion generation module and the emulsion rheology 445 is determined, the method 400 further includes a step of formulating computational algorithms 450 for the equation of state 425 and the emulsion rheology 445. The method 400 further includes a step of formulating a 3-D compositional reservoir simulation model 455 as represented by the geostatic data 401 and the computational algorithms 450 to simulate an enhanced and/or improved oil recovery process of the reservoir using the emulsion. The simulation will provide data regarding how the emulsion is transported to the reservoir and how the emulsion stimulates the reservoir.

After the simulation is run in the 3-D compositional reservoir simulation model 455, the method 400 further includes a step running multiple simulations 460 of different types of emulsions generated by the emulsion generation module 431 to gather enough data from the simulations to determine which emulsion will achieve an optimum hydrocarbon recovery in the reservoir.

The method 400 also includes a core displacement module 470. In the core displacement module 470, one or more core displacement tests are run on one or more representative reservoir cores that are adjusted to residual oil conditions at reservoir temperature and pressure and simulate actual post water flooding conditions. Residual oil in each representative reservoir core is then displaced at reservoir pressure and temperature conditions with one or more of the emulsions to evaluate the displacement efficiency of the emulsions. Additional representative reservoir cores can also be displaced with carbon dioxide and other enhanced and/or improved oil recovery fluids for comparison with the representative reservoir cores that are displaced with the emulsions to determine which one provides the optimum fluid displacement.

The method 400 also includes a field displacement module 480. In the field displacement module 480, one or more field displacement tests are run to demonstrate the enhanced and/or improved oil recovery displacement efficiency of one or more of the emulsions along with associated costs under actual reservoir conditions. A field displacement test utilizes two or more wells wherein at least one well is an injection well and one well is a production well. The injection and production wells may either currently exist or are specifically drilled and completed in the reservoir of interest typically on close spacing to reduce response time and fluid costs. A volume (e.g. 30%-50% pore volume) of emulsion is injected under reservoir conditions with a specified injection protocol through the injection well and then displaced with a volume (e.g. 50%-70% pore volume) of a final displacement fluid, which may include carbon dioxide, nitrogen, natural gas, methane, LNG, ethane, water, viscosified water, formation water, and/or combinations thereof. The fluids, including formation oil, are displaced and produced back to the surface via the production well.

Figure 5:
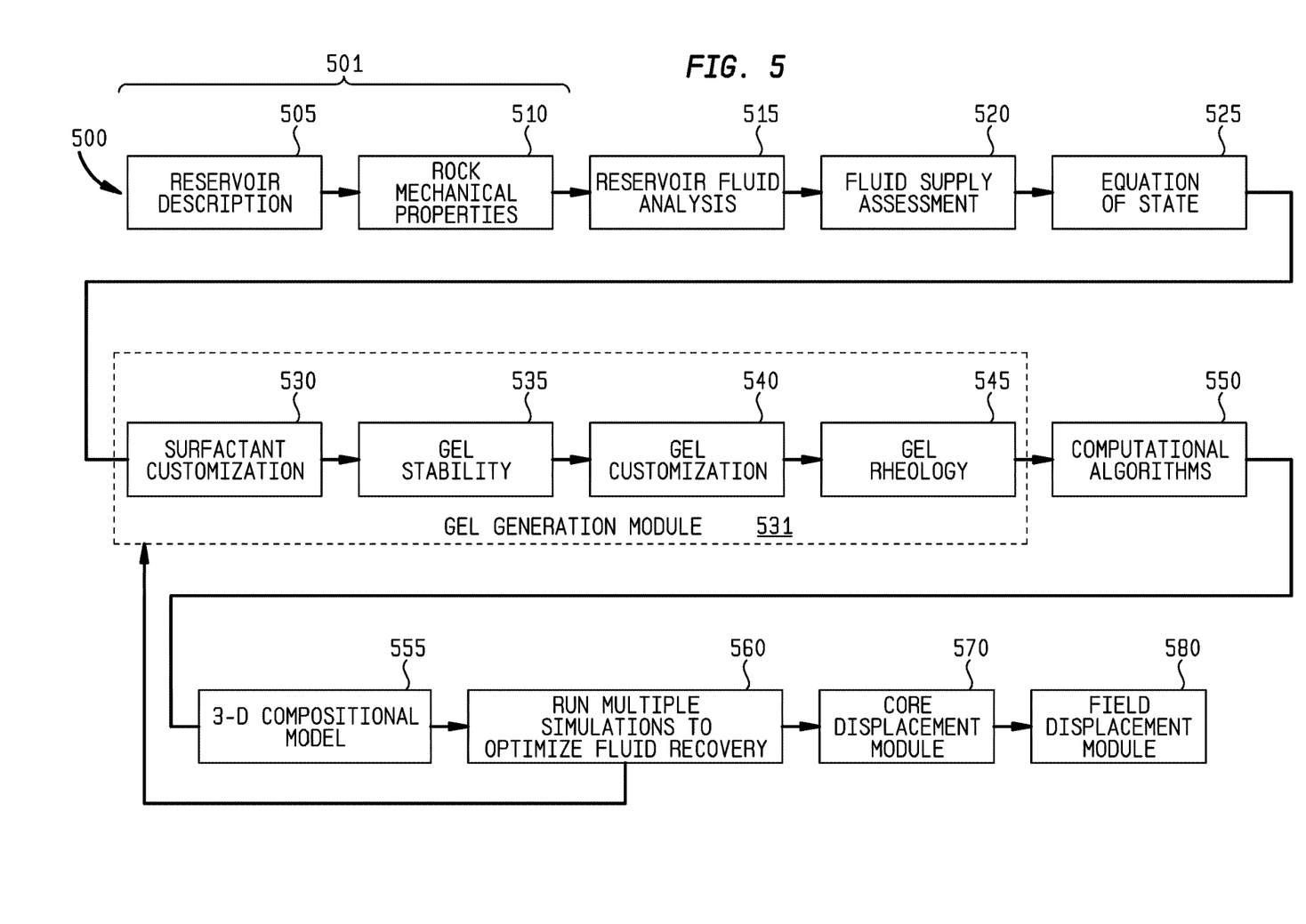
FIG. 5 is a schematic view of a method for optimizing gelled based Y-Grade NGL enhanced oil recovery fluids according to one embodiment.

FIG. 5 is a schematic view of a method 500 for optimizing gelled based Y-Grade NGL enhanced oil recovery fluids according to one embodiment.

The method 500 includes the steps of gathering geostatic data 501 of a subsurface formation, such as a hydrocarbon bearing reservoir, and conducting a reservoir fluid analysis 515 to gather data regarding the reservoir fluid properties, similar to the steps of gathering geostatic data 201 and conducting a reservoir fluid analysis 215 in the method 200.

The method 500 further includes a step of assessing the availability of a supply of fluids 520 needed to create the gelled based Y-Grade NGL enhanced oil recovery fluids. To create a gelled fluid, the fluid 520 will comprise Y-Grade NGL and a gelling agent. An assessment is made to determine the quantity and/or composition of the Y-Grade NGL and/or the gelling agent that is available for forming the gelled based Y-Grade NGL enhanced oil recovery fluids.

The method 500 further includes a step of determining an equation of state 525 based on the reservoir fluid analysis 515 and the assessment of the supply of fluids 520. The equation of state 525 may be based on the reservoir fluid data and the quantity and/or composition of the Y-Grade NGL and/or the gelling agent.

The method 500 further includes a step of generating a gelled enhanced oil recovery fluid through a gel generation module 531. The gel generation module 531 includes one or more of the steps of customizing a gelling agent 530 to be mixed with the Y-Grade NGL to form the gelled enhanced oil recovery fluid, adjusting gel stability 535 of the gelled enhanced oil recovery fluid, customizing the gelled enhanced oil recovery fluid 540, and determining a gel rheology 545 of the gelled enhanced oil recovery fluid.

The step of customizing the gelling agent 530 may include selecting at least one of hydrocarbon soluble copolymers, phosphate esters, organo-metallic complex cross-linkers, amine carbamates, alumunin soaps, cocoamine (C12-C14), sebacoyl chloride, oley (C18) amine, toulen-2,4-diisocyanate, tolune-2,6-diisolcyanate, and combinations thereof as the gelling agent.

The step of adjusting gel stability 535 includes several ways of changing the stability of the gelled enhanced oil recovery fluid. The stability of the gelled enhanced oil recovery fluid may be adjusted by changing at least one of the type of gelling agent and the concentration of the gelling agent used to form the gelled enhanced oil recovery fluid.

The step of customizing the gelled enhanced oil recovery fluid 540 includes adding a secondary fluid to the gelled enhanced oil recovery fluid. The secondary fluid may comprise at least one of aromatics, alkanes, and crude oil. Aromatics may comprise at least one of benzene, naphtha, xylene, toluene, fuel oils, olefins, and diesel. Alkanes may comprise at least one of heptane, octane, and hexane. Crude oil may comprise at least one of NGL's, condensate, light oil, medium oil, and reservoir oil.

The step of determining gel rheology 545 includes determining the rheology of the gelled enhanced oil recovery fluid. The gel rheology 545 may be defined by, including but not limited to, its apparent viscosity, density, wettability, relative permeability of the gel, and saturation of the gel as a function of temperature, pressure, and composition of the gel.

After the gelled enhanced oil recovery fluid is generated by the gel generation module 531 and the gel rheology 545 is determined, the method 500 further includes a step of formulating computational algorithms 550 for the equation of state 525 and the gel rheology 545. The method 500 further includes a step of formulating a 3-D compositional reservoir simulation model 555 as represented by the geostatic data 501 and the computational algorithms 550 to simulate an enhanced and/or improved oil recovery process of the reservoir using the gelled enhanced oil recovery fluid.

After the simulation is run in the 3-D compositional reservoir simulation model 555, the method 500 further includes a step running multiple simulations 560 of different types of gelled enhanced oil recovery fluids generated by the gel generation module 531 to gather enough data from the simulations to determine which gelled enhanced oil recovery fluid will achieve an optimum hydrocarbon recovery in the reservoir.

The method 500 also includes a core displacement module 570. In the core displacement module 570, one or more core displacement tests are run on one or more representative reservoir cores that are adjusted to residual oil conditions at reservoir temperature and pressure and simulate actual post water flooding conditions. Residual oil in each representative reservoir core is then displaced at reservoir pressure and temperature conditions with one or more of the gelled enhanced oil recovery fluids to evaluate the displacement efficiency of the gelled enhanced oil recovery fluids. Additional representative reservoir cores can also be displaced with carbon dioxide and other enhanced and/or improved oil recovery fluids for comparison with the representative reservoir cores that are displaced with the gelled enhanced oil recovery fluids to determine which one provides the optimum fluid displacement.

The method 500 also includes a field displacement module 580. In the field displacement module 580, one or more field displacement tests are run to demonstrate the enhanced and/or improved oil recovery displacement efficiency of one or more of the gelled enhanced oil recovery fluids along with associated costs under actual reservoir conditions. A field displacement test utilizes two or more wells wherein at least one well is an injection well and one well is a production well. The injection and production wells may either currently exist or are specifically drilled and completed in the reservoir of interest typically on close spacing to reduce response time and fluid costs. A volume (e.g. 30%-50% pore volume) of gelled enhanced oil recovery fluid is injected under reservoir conditions with a specified injection protocol through the injection well and then displaced with a volume (e.g. 50%-70% pore volume) of a final displacement fluid, which may include carbon dioxide, nitrogen, natural gas, methane, LNG, ethane, water, viscosified water, formation water, and/or combinations thereof. The fluids, including formation oil, are displaced and produced back to the surface via the production well.

The supply of Y-Grade NGL may be provided in Y-Grade NGL storage tanks that comprise of onsite Y-Grade NGL pressurized storage vessels that are supplied from a regional Y-Grade NGL gathering pipeline, a regional gas splitter, or a gas processing facility via tanker trucks.

The enhanced oil recovery fluids, such as the hydrocarbon foam, the emulsion based foam, the emulsion, and the gelled enhanced oil recovery fluid, disclosed herein may comprise non-aqueous based chemical agents. The non-aqueous based chemical agents include but are not limited to non-aqueous based foaming agents, foam stabilizers, emulsifying agents, gelling agents, viscosity increasing agents, surfactants, nanoparticles, and combinations thereof.

The enhanced oil recovery fluids, such as the emulsion based foam and the emulsion, disclosed herein may comprise aqueous based chemical agents. The aqueous based chemical agents include but are not limited to aqueous based foaming agents, foam stabilizers, emulsifying agents, gelling agents, viscosity increasing agents, surfactants, nanoparticles, breakers, friction reducers, scale inhibitors, biocides, acids, buffer/pH adjusting agents, clay stabilizers, corrosion inhibitors, crosslinkers, iron controls, solvents, and combinations thereof.

The enhanced oil recovery fluids, such as the hydrocarbon foam and the emulsion based foam, disclosed herein may comprise foaming agents. The foaming agents include but are not limited to nonionic surfactants, wherein the nonionic surfactants comprise at least one of a siloxane surfactant, a fluorosurfactant, a fatty acid ester, a glyceride, a silicon emulsifier, a hydrophobic silica powder, and combinations thereof.

The foaming agents may also include but are not limited to surfactants, such as anionic surfactants, wherein the anionic surfactants include iC90-glycol, iC10-glycol, 1-propanol, iso-propanol, 2-butanol, butyl glycol, sulfonic acids, betaine compounds, fluorosurfactants, hydrocarbon solvents, aluminum soaps, phosphate esters, alcoholethersulfates, alcohol sulfate, alcylsulfates, isethionates, sarconisates, acylsarcosinates, olefinsulfonates, alcylethercarboxylates, alcylalcoholam ides, aminoxids, alkylbenzolsulfonate, alkylnaphthalene sulfonates, fattyalcohol ethoxylates, oxo-alcohol ethoxylates, alkylethoxylates, alkylphenolethoxylates, fattyamin- and fattyamidethoxylates, alkylpolyglucosides, oxoalcohol ethoxylates, guerbetalcohol alkoxylates, alkylethersulfonate, EO/PO blockpolymers, betaines, cocamidopropylbetaine, C8-C10 alkylam idopropylbetaine, sulfobetaines, alkenylsulfonates, alkylglykols, alcoholalkoxylates, sulfosuccinates, alkyletherphosphates, esterquats, dialcylammoniumderivatives, trialcylammoniumderivatives, and combinations thereof.

The enhanced oil recovery fluids, such as the hydrocarbon foam and the emulsion based foam, disclosed herein may comprise foam stabilizers. The foam stabilizers include but are not limited to proteins, microparticles, nanoparticles, silica, and silica derivatives that are known to stabilize foam and emulsions through so-called "pickering". The foam stabilizers may comprise additives that increase the viscosity of the enhanced oil recovery fluid composing the lamella, such as polymeric structures.

The enhanced oil recovery fluids, such as the gelled enhanced oil recovery fluids, disclosed herein may comprise gelling agents. The gelling agents include but are not limited to hydrocarbon soluble copolymers, phosphate esters, organo-metallic complex cross-linkers, amine carbamates, aluminum soaps, cocoamine (C12-C14), sebacoyl chloride, oley (C18) amine, toulen-2,4-diisocyanate, tolune-2,6-diisolcyanate, and combinations thereof.

The enhanced oil recovery fluids, such as the hydrocarbon foam, the emulsion based foam, the emulsion, and the gelled enhanced oil recovery fluids, disclosed herein may comprise secondary fluids. The secondary fluids include but are not limited to aromatics, alkanes, crude oils, and combinations thereof. The secondary fluid may comprises 10% or less by volume of the enhanced oil recovery fluids described herein. The aromatics may comprise at least one of benzene, naphtha, xylene, toluene, fuel oils, olefins, and diesel. The alkanes may comprise at least one of heptane, octane, and hexane. The crude oil may comprise at least one of NGL's, condensate, light oil, medium oil, and reservoir oil.

The enhanced oil recovery fluids disclosed herein may comprise an unfractionated hydrocarbon mixture comprising ethane, propane, butane, isobutane, and pentane plus, wherein the ethane, propane, and butane comprise at least 75% by volume of the unfractionated hydrocarbon mixture.

The enhanced oil recovery fluids disclosed herein may comprise an unfractionated hydrocarbon mixture comprising ethane, propane, butane, isobutane, and pentane plus, wherein the ethane comprises at least 3% by volume of the unfractionated hydrocarbon mixture.

The enhanced oil recovery fluids may comprise an unfractionated hydrocarbon mixture comprising ethane, propane, butane, isobutane, and pentane plus, wherein the pentane plus comprises less than 30% by volume of the unfractionated hydrocarbon mixture.

The enhanced oil recovery fluids disclosed herein may be formed with any type of gas, such as carbon dioxide, nitrogen, natural gas, methane, LNG, and/or ethane, and include one or more foaming agents, such as a surfactant, to form a hydrocarbon foam. The gas content of the enhanced oil recovery fluid may be between about 55% to about 95% by volume.

While the foregoing is directed to certain embodiments, other and further embodiments may be devised without departing from the basic scope thereof, and the scope thereof is determined by the claims that follow.

The invention claimed is:

1. A method of optimizing a Y-Grade NGL enhanced oil recovery fluid, comprising:
gathering geostatic data and reservoir fluid data of a hydrocarbon bearing reservoir;
determining a quantity and composition of a supply of Y-Grade NGL and a gas;
generating an equation of state based on the reservoir fluid data and data regarding the composition of the supply of Y-Grade NGL and the gas;
generating a simulated hydrocarbon foam through a foam generation module, wherein the foam generation module is configured to customize a surfactant to be mixed with the Y-Grade NGL and the gas to form the hydrocarbon foam, adjust foam stability of the hydrocarbon foam, select a secondary fluid to add to the hydrocarbon foam, and determine a foam rheology of the hydrocarbon foam;

simulating an oil recovery process of the reservoir using the hydrocarbon foam through a 3-D compositional reservoir simulation model, wherein the geostatic data, previously matched historical production and pressure data, the equation of state, and the foam rheology are input into the model to simulate the oil recovery process of the reservoir using the hydrocarbon foam; and running multiple simulations of the oil recovery process of the reservoir through the model for different simulated hydrocarbon foams generated by the foam generation module to determine which hydrocarbon foam will obtain an optimum fluid recovery.

2. The method of claim 1, further comprising customizing the surfactant by selecting at least one of a siloxane surfactant, a fluorosurfactant, a fatty acid ester, a glyceride, a silicon emulsifier, and a hydrophobic silica powder as the surfactant.

3. The method of claim 1, further comprising customizing the surfactant by at least one of adjusting the molecular weight of the surfactant, selecting a surfactant that is soluble in light hydrocarbons, and adjusting the concentration of surfactant by up to 5% by weight of the liquid phase of the hydrocarbon foam.

4. The method of claim 1, further comprising adjusting foam stability by performing at least one of the following steps: adjusting foam quality based on the amount of the gas used to form the hydrocarbon foam, adding nanoparticles to reduce fluid loss of the liquid phase of the hydrocarbon foam, adding a hydrocarbon soluble co-polymer to viscosify the liquid phase of the hydrocarbon foam, and changing the type of gas used to form the hydrocarbon foam.

5. The method of claim 1, wherein the secondary fluid comprises at least one of aromatics, alkanes, and crude oil.

6. The method of claim 5, wherein the crude oil comprises at least one of NGL's, condensate, light oil, medium oil, and reservoir oil.

7. The method of claim 1, further comprising adjusting foam stability by adjusting foam quality, wherein the foam quality is adjusted by adjusting the amount of gas used to form the hydrocarbon foam.

8. The method of claim 1, further comprising adjusting foam stability by adjusting apparent viscosity, wherein the apparent viscosity is adjusted by at least one of the following: adjusting foam quality based on the amount of the gas used to form the hydrocarbon foam, adding a hydrocarbon soluble co-polymer to viscosify the liquid phase of the hydrocarbon foam, and adding a secondary fluid comprising up to 10% of the liquid phase of the hydrocarbon foam, wherein the secondary fluid comprises at least one of aromatics, alkanes, and crude oil.

9. The method of claim 1, further comprising determining the foam rheology based on apparent viscosity, density, wettability, relative permeability of the hydrocarbon foam, and saturation of the hydrocarbon foam as a function of temperature, pressure, and composition of the hydrocarbon foam.

10. The method of claim 1, further comprising formulating computational algorithms for the equation of state and the foam rheology for each hydrocarbon foam.

11. The method of claim 1, wherein the gas comprises at least one of nitrogen, carbon dioxide, natural gas, methane, LNG, and ethane.

12. The method of claim 1, further comprising conducting a core displacement test on a representative core by displacing residual oil in the representative core using one or more of the hydrocarbon foams to determine the displacement efficiency of the hydrocarbon foams, and conducting a field displacement test by injecting at least one of the hydrocarbon foams through an injection well into the hydrocarbon bearing reservoir and then displacing the hydrocarbon foam with a final displacement fluid to demonstrate the displacement efficiency of the hydrocarbon foam.

13. A method of optimizing a Y-Grade NGL enhanced oil recovery fluid, comprising:

gathering geostatic data and reservoir fluid data of a hydrocarbon bearing reservoir;

determining a quantity and composition of a supply of Y-Grade NGL, a gas, and water;

generating an equation of state based on the reservoir fluid data and data regarding the composition of the supply of Y-Grade NGL, the gas, and the water;

generating a simulated emulsion based foam through an emulsion based foam generation module, wherein the emulsion based foam generation module is configured to customize a surfactant to be mixed with the Y-Grade NGL, the gas, and the water to form the emulsion based foam, adjust foam stability of the emulsion based foam, select a secondary fluid to add to the emulsion based foam, and determine an emulsion based foam rheology of the emulsion based foam;

simulating an oil recovery process of the reservoir using the emulsion based foam through a 3-D compositional reservoir simulation model, wherein the geostatic data, previously matched historical production and pressure data, the equation of state, and the emulsion based foam rheology are input into the model to simulate the oil recovery process of the reservoir using the emulsion based foam; and running multiple simulations of the oil recovery process of the reservoir through the model for different simulated emulsion based foams generated by the emulsion based foam generation module to determine which emulsion based foam will obtain an optimum fluid recovery.

14. The method of claim 13, wherein the surfactant acts as a foaming agent, an emulsifying agent, or both.

15. The method of claim 13, further comprising customizing the surfactant by at least one of adjusting the molecular weight of the surfactant and adjusting the concentration of surfactant by up to 5% by weight of the liquid phase of the emulsion based foam.

16. The method of claim 13, further comprising customizing the surfactant by selecting at least one of a non-ionic surfactant, an anionic surfactant, and a cationic surfactant as the surfactant, wherein the non-ionic surfactant is soluble in light hydrocarbons, and wherein the anionic surfactant and the cationic surfactants are soluble in water.

17. The method of claim 16, wherein the non-ionic surfactant comprises at least one of a siloxane, a fluorosurfactant, a fatty acid ester, a glyceride, a silicon emulsifier, and a hydrophobic silica powder as the surfactant.

18. The method of claim 13, further comprising adjusting foam stability by performing at least one of the following steps: adjusting foam quality based on the amount of the gas used to form the emulsion based foam, adding nanoparticles to reduce fluid loss of the liquid phase of the emulsion based foam, adding a hydrocarbon soluble co-polymer to viscosify the liquid phase of the emulsion based foam, adding a water soluble co-polymer to viscosify the liquid phase of the emulsion based foam, and changing the type of gas used to form the emulsion based foam.

19. The method of claim 13, wherein the secondary fluid comprises at least one of aromatics, alkanes, and crude oil.

20. The method of claim 19, wherein the crude oil comprises at least one of NGL's, condensate, light oil, medium oil, and reservoir oil.

21. The method of claim 13, further comprising adjusting foam stability by adjusting foam quality, wherein the foam quality is adjusted by adjusting the amount of gas used to form the emulsion based foam.

22. The method of claim 13, further comprising further comprising adjusting foam stability by adjusting apparent viscosity, wherein the apparent viscosity is adjusted by at least one of the following: adjusting foam quality based on the amount of the gas used to form the emulsion based foam, adding a hydrocarbon soluble co-polymer to viscosify the liquid phase of the emulsion based foam, adding a water soluble co-polymer to viscosify the liquid phase of the emulsion based foam, and adding a secondary fluid comprising up to 10% of the liquid phase of the emulsion based foam, wherein the secondary fluid comprises at least one of aromatics, alkanes, and crude oil.

23. The method of claim 13, further comprising determining the emulsion based foam rheology based on apparent viscosity, density, wettability, relative permeability of the emulsion based foam, and saturation of the emulsion based foam as a function of temperature, pressure, and composition of the emulsion based foam.

24. The method of claim 13, further comprising formulating computational algorithms for the equation of state and the emulsion based foam rheology for each emulsion based foam.

25. The method of claim 13, wherein the water is formation water, brine, or seawater and comprises up to 10% of the liquid phase of the emulsion based foam.

26. The method of claim 13, wherein the water is potassium chloride water and comprises up to 10% of the liquid phase of the emulsion based foam, wherein the potassium chloride water comprises up to 4% potassium chloride.

27. The method of claim 13, wherein the gas comprises at least one of nitrogen, carbon dioxide, natural gas, methane, LNG, and ethane.

28. The method of claim 13, further comprising conducting a core displacement test on a representative core by displacing residual oil in the representative core using one or more of the emulsion based foams to determine the displacement efficiency of the emulsion based foams, and conducting a field displacement test by injecting at least one of the emulsion based foams through an injection well into the hydrocarbon bearing reservoir and then displacing the emulsion based foam with a final displacement fluid to demonstrate the displacement efficiency of the emulsion based foam.

29. A method of optimizing a Y-Grade NGL enhanced oil recovery fluid, comprising:
gathering geostatic data and reservoir fluid data of a hydrocarbon bearing reservoir;
determining a quantity and composition of a supply of Y-Grade NGL and water;
generating an equation of state based on the reservoir fluid data and data regarding the composition of the supply of Y-Grade NGL and the water;
generating a simulated emulsion through an emulsion generation module, wherein the emulsion generation module is configured to customize a surfactant to be mixed with the Y-Grade NGL and the water to form the emulsion, adjust stability of the emulsion, customize the emulsion, and determine a rheology of the emulsion;
simulating an oil recovery process of the reservoir using the emulsion through a 3-D compositional reservoir simulation model, wherein the geostatic data, previously matched historical production and pressure data, the equation of state, and the emulsion rheology are input into the model to simulate the oil recovery process of the reservoir using the emulsion; and
running multiple simulations of the oil recovery process of the reservoir through the model for different simulated emulsions generated by the emulsion generation module to determine which emulsion will obtain an optimum fluid recovery.

30. The method of claim 29, further comprising customizing the surfactant by selecting at least one of a siloxane surfactant, a fluorosurfactant, a fatty acid ester, a glyceride, a silicon emulsifier, and a hydrophobic silica powder as the surfactant.

31. The method of claim 29, further comprising customizing the surfactant by at least one of adjusting the molecular weight of the surfactant, selecting a non-ionic surfactant that is selectively soluble in light hydrocarbons, selecting an anionic surfactant that is selectively soluble in water, selecting a cationic surfactant that is selectively soluble in water, and adjusting the concentration of surfactant by up to 5% by weight of the emulsion.

32. The method of claim 29, further comprising customizing the emulsion by changing the percent volume of water used to form the emulsion.

33. The method of claim 29, further comprising customizing the emulsion by adding a secondary fluid to the emulsion, wherein the secondary fluid comprises at least one of aromatics, alkanes, and crude oil.

34. The method of claim 33, wherein the crude oil comprises at least one of NGL's, condensate, light oil, medium oil, and reservoir oil.

35. The method of claim 29, further comprising customizing the emulsion by adjusting the apparent viscosity, wherein the apparent viscosity is adjusted by at least one of the following: adding a hydrocarbon soluble co-polymer to viscosify the liquid phase of the emulsion, adding a water soluble co-polymer to viscosify the liquid phase of the emulsion, changing the percent volume of water used to form the emulsion, and adding a secondary fluid comprising up to 10% of the liquid phase of the emulsion, wherein the secondary fluid comprises at least one of aromatics, alkanes, and crude oil.

36. The fluid of claim 29, further comprising customizing the emulsion by adding a viscosifier, wherein the viscosifier comprises at least one of a hydrocarbon soluble co-polymer and a water soluble viscosifier, and wherein the water soluble viscosifer comprises at least one of water soluble co-polymers, polysaccarides, guar gum, viscoelastic surfactants, crosslinkers, cellulosic viscosifiers, and hydroxyethyl cellulose.

37. The method of claim 29, further comprising determining the emulsion rheology based on apparent viscosity, density, wettability, relative permeability of the emulsion, and saturation of the emulsion as a function of temperature, pressure, and composition of the emulsion.

38. The method of claim 29, further comprising formulating computational algorithms for the equation of state and the emulsion rheology for each emulsion.

39. The method of claim 29, further comprising conducting a core displacement test on a representative core by displacing residual oil in the representative core using one or more of the emulsions to determine the displacement efficiency of the emulsions, and conducting a field displacement test by injecting at least one of the emulsions through an injection well into the hydrocarbon bearing reservoir and then displacing the emulsion with a final displacement fluid to demonstrate the displacement efficiency of the emulsion.

40. The method of claim 29, wherein the water is formation water, brine or seawater and comprises up to 10% of the liquid phase of the emulsion.

41. The method of claim 29, wherein the water is potassium chloride water and comprises up to 10% of the liquid phase of the emulsion, wherein the potassium chloride water comprises up to 4% potassium chloride.

42. A method of optimizing a Y-Grade NGL enhanced oil recovery fluid, comprising:
gathering geostatic data and reservoir fluid data of a hydrocarbon bearing reservoir;
determining a quantity and composition of a supply of Y-Grade NGL;
generating an equation of state based on the reservoir fluid data and data regarding the composition of the supply of Y-Grade NGL;
generating a simulated gelled enhanced oil recovery fluid through a gel generation module, wherein the gel generation module is configured to select a gelling agent to be mixed with the Y-Grade NGL to form the gelled enhanced oil recovery fluid, adjust gel stability of the gelled enhanced oil recovery fluid, select a secondary fluid to add to the gelled enhanced oil recovery fluid, and determine a gel rheology of the gelled enhanced oil recovery fluid;
simulating an oil recovery process of the reservoir using the gelled enhanced oil recovery fluid through a 3-D compositional reservoir simulation model, wherein the geostatic data, previously matched historical production and pressure data, the equation of state, and the foam rheology are input into the model to simulate the oil recovery process of the reservoir using the gelled enhanced oil recovery fluid; and
running multiple simulations of the oil recovery process of the reservoir through the model for different simulated gelled enhanced oil recovery fluids generated by the gel generation module to determine which gelled enhanced oil recovery fluid will obtain an optimum fluid recovery.

43. The method of claim 42, wherein the gelling agent is selected from at least one of hydrocarbon soluble copolymers, phosphate esters, organo-metallic complex cross-linkers, amine carbamates, aluminum soaps, cocoamine (C12-C14), sebacoyl chloride, oley (C18) amine, toulen-2, 4-diisocyanate, tolune-2, 6-diisolcyanate, and combinations thereof.

44. The method of claim 42, further comprising adjusting gel stability by changing at least one of the type of gelling agent and the concentration of the gelling agent.

45. The method of claim 42, wherein the secondary fluid comprises at least one of aromatics, alkanes, and crude oil.

46. The method of claim 45, wherein the crude oil comprises at least one of NGL's, condensate, light oil, medium oil, and reservoir oil.

47. The method of claim 42, further comprising determining the gel rheology based on apparent viscosity, density, wettability, relative permeability of the gelled enhanced oil recovery fluid, and saturation of the gelled enhanced oil recovery fluid as a function of temperature, pressure, and composition of the gelled enhanced oil recovery fluid.

48. The method of claim 42, wherein the Y-Grade NGL comprises an unfractionated hydrocarbon mixture comprising ethane, propane, butane, isobutane, and pentane plus, wherein the unfractionated hydrocarbon mixture is a byproduct of a condensed and de-methanized hydrocarbon stream, wherein the unfractionated hydrocarbon mixture is condensed out of the hydrocarbon stream at a temperature at or below 0 degrees Fahrenheit, wherein the unfractionated hydrocarbon mixture comprises ethane, propane, and butane in an amount of at least 75% by volume, and wherein the unfractionated hydrocarbon mixture comprises pentane plus in an amount less than 30% by volume.

49. The method of claim 42, wherein running multiple simulations comprises generating different gelled enhanced oil recovery fluid fluids though the gel generation module, formulating computational algorithms for each gelled enhanced oil recovery fluid based on the equation of state and gel rheology of each gelled enhanced oil recovery fluid, and simulating the oil recovery process of the reservoir using the gelled enhanced oil recovery fluid through 3-D compositional reservoir simulation model to gather enough data to determine which gelled enhanced oil recovery fluid will achieve the optimum fluid recovery.

50. The method of claim 42, further comprising conducting a core displacement test on a representative core by displacing residual oil in the representative core using one or more of the gelled enhanced oil recovery fluids to determine the displacement efficiency of the gelled enhanced oil recovery fluids, and conducting a field displacement test by injecting at least one of the gelled enhanced oil recovery fluids through an injection well into the hydrocarbon bearing reservoir and then displacing the gelled enhanced oil recovery fluid with a final displacement fluid to demonstrate the displacement efficiency of the gelled enhanced oil recovery fluid.

* * * * *